United States Patent
Nair et al.

(10) Patent No.: US 9,855,020 B2
(45) Date of Patent: Jan. 2, 2018

(54) ADAPTIVE INTERFACE FOR A MEDICAL IMAGING SYSTEM

(71) Applicant: Volcano Corporation, San Diego, CA (US)

(72) Inventors: Anuja Nair, Bedford, MA (US); Andrew Hancock, Sacramento, CA (US)

(73) Assignee: VOLCANO CORPORATION, San Diego, CA (US)

( * ) Notice: Subject to any disclaimer, the term of this patent is extended or adjusted under 35 U.S.C. 154(b) by 158 days.

(21) Appl. No.: 14/841,398

(22) Filed: Aug. 31, 2015

(65) Prior Publication Data

US 2015/0366534 A1    Dec. 24, 2015

Related U.S. Application Data

(63) Continuation of application No. 14/137,414, filed on Dec. 20, 2013, now Pat. No. 9,121,926.

(Continued)

(51) Int. Cl.
*A61B 8/12* (2006.01)
*G01S 7/52* (2006.01)
(Continued)

(52) U.S. Cl.
CPC .............. *A61B 8/12* (2013.01); *A61B 6/12* (2013.01); *A61B 8/06* (2013.01); *A61B 8/0841* (2013.01);
(Continued)

(58) Field of Classification Search
CPC combination set(s) only.
See application file for complete search history.

(56) References Cited

U.S. PATENT DOCUMENTS 5,321,455 A   6/1994  Cocca et al.
5,882,333 A * 3/1999  Schaer .............. A61M 25/0144
                                                        600/434

(Continued)

FOREIGN PATENT DOCUMENTS

JP    2008-46849 A    2/2008
JP    2012/523910    10/2012

(Continued)

OTHER PUBLICATIONS

International Searching Authority/European Patent Office, Supplementary European Search Report for European application No. 13865806.7, dated Jun. 17, 2016, 7 pages.

(Continued)

*Primary Examiner* — Anand Bhatnagar

(57) ABSTRACT

Intravascular devices, systems, and methods are provided. In one embodiment, an intravascular system includes an intravascular device and a computing device in communication with the intravascular device, the computing device operable to: present a set of mode options to a user at a user display device; receive a mode selection from the presented set of mode options; determine a set of operating parameters based on the mode selection; receive a first set of medical sensing data; and process the first set of medical sensing data according to the operating parameters, wherein the computing device is further operable to determine the set of operating parameters based on at least one of a previous mode selection, a user preference, an operative course of a medical procedure, patient information, the first set of medical sensing data, a second set of medical sensing data, a status indicator, or a sensing device identifier.

12 Claims, 5 Drawing Sheets

Related U.S. Application Data

(60) Provisional application No. 61/745,518, filed on Dec. 21, 2012.

(51) Int. Cl.

| | | |
|---|---|---|
| *A61B 8/06* | (2006.01) | |
| *A61B 8/08* | (2006.01) | |
| *A61B 8/00* | (2006.01) | |
| *A61B 6/12* | (2006.01) | |
| *A61B 5/00* | (2006.01) | |
| *A61B 5/0215* | (2006.01) | |
| *A61B 5/027* | (2006.01) | |
| *A61B 5/0402* | (2006.01) | |

(52) U.S. Cl.
CPC .......... *A61B 8/0883* (2013.01); *A61B 8/0891* (2013.01); *A61B 8/445* (2013.01); *A61B 8/463* (2013.01); *A61B 8/464* (2013.01); *A61B 8/465* (2013.01); *A61B 8/467* (2013.01); *A61B 8/52* (2013.01); *A61B 8/54* (2013.01); *G01S 7/52098* (2013.01); *A61B 5/0066* (2013.01); *A61B 5/0084* (2013.01); *A61B 5/027* (2013.01); *A61B 5/0215* (2013.01); *A61B 5/0402* (2013.01); *A61B 5/743* (2013.01); *A61B 8/4438* (2013.01)

(56) References Cited

U.S. PATENT DOCUMENTS

| | | |
|---|---|---|
| 5,921,931 A | 7/1999 | O'Donnell et al. |
| 6,083,170 A * | 7/2000 | Ben-Haim ............ A61B 5/0422 600/462 |
| 6,200,268 B1 | 3/2001 | Vince et al. |
| 6,381,350 B1 | 4/2002 | Klingensmith et al. |
| 6,690,961 B1 | 2/2004 | Kaufman et al. |
| 6,801,916 B2 | 10/2004 | Robergé et al. |
| 7,074,188 B2 | 7/2006 | Nair et al. |
| 7,088,798 B2 | 8/2006 | Chen et al. |
| 7,130,457 B2 | 10/2006 | Kaufman et al. |
| 7,175,597 B2 | 2/2007 | Vince et al. |
| 7,371,067 B2 | 5/2008 | Anderson et al. |
| 7,591,788 B2 | 9/2009 | Phillips et al. |
| 7,769,602 B2 | 8/2010 | Motoki |
| 8,027,986 B2 | 9/2011 | Bay et al. |
| 8,187,191 B2 | 5/2012 | Hancock et al. |
| 8,286,079 B2 | 10/2012 | Song et al. |
| 8,797,155 B2 | 8/2014 | Huennekens et al. |
| 2004/0021693 A1 | 2/2004 | Monteleone |
| 2004/0109028 A1* | 6/2004 | Stern .................... G06F 19/3412 715/771 |
| 2007/0016028 A1* | 1/2007 | Donaldson ........... A61B 8/0833 600/437 |
| 2007/0016029 A1 | 1/2007 | Donaldson et al. |
| 2008/0072151 A1* | 3/2008 | Song .................... G06F 3/0481 715/708 |
| 2009/0276725 A1 | 11/2009 | Glaser-Seidnitzer et al. |
| 2010/0128946 A1 | 5/2010 | Fidrich et al. |
| 2010/0174190 A1 | 7/2010 | Hancock et al. |
| 2011/0263985 A1* | 10/2011 | Gauthier .................. A61B 8/06 600/454 |
| 2012/0157844 A1* | 6/2012 | Halmann ............. A61B 8/0841 600/443 |
| 2012/0220874 A1 | 8/2012 | Hancock et al. |
| 2013/0303907 A1 | 11/2013 | Corl et al. |
| 2014/0039305 A1* | 2/2014 | Wenderow ............... A61B 6/12 600/424 |
| 2014/0056099 A1 | 2/2014 | Hancock et al. |
| 2014/0066765 A1* | 3/2014 | Fan .......................... A61B 8/06 600/440 |
| 2014/0142398 A1* | 5/2014 | Patil ....................... A61B 6/463 600/301 |
| 2014/0350404 A1 | 11/2014 | Rajguru et al. |
| 2016/0346048 A1* | 12/2016 | Wenderow ............... A61B 6/12 |

FOREIGN PATENT DOCUMENTS

| | | |
|---|---|---|
| KR | 10-2011/0132192 | 12/2011 |
| WO | WO 2008/008991 A2 | 1/2008 |

OTHER PUBLICATIONS

International Search Report and Written Opinion received in corresponding Patent Cooperation Treaty Application No. PCT/US2013/076336 dated Apr. 23, 2014, 9 pages.

* cited by examiner

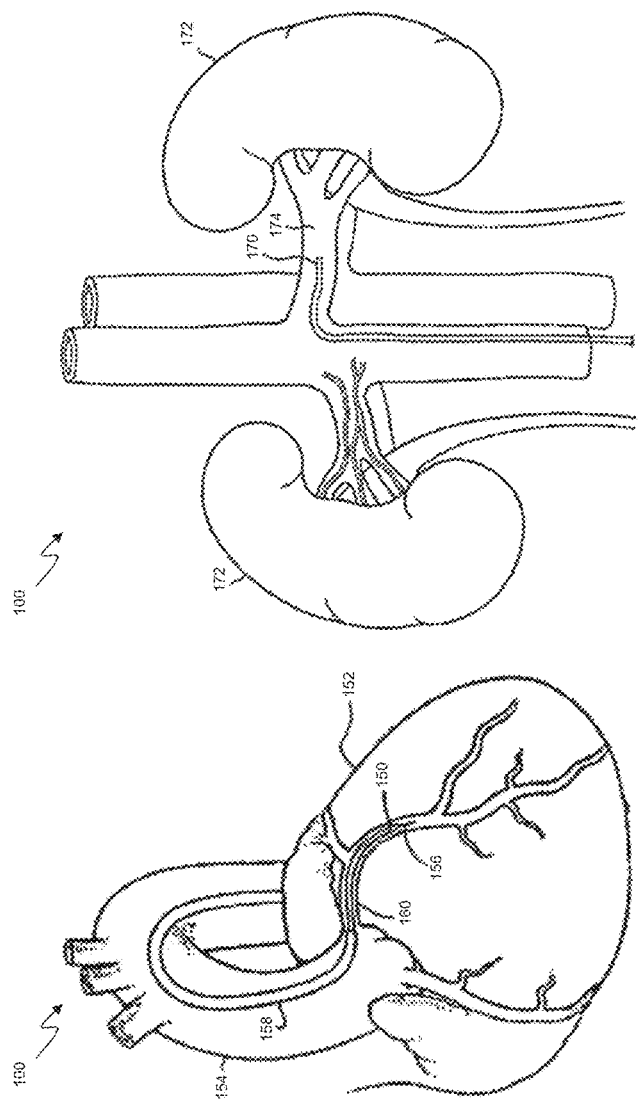

ADAPTIVE INTERFACE FOR A MEDICAL IMAGING SYSTEM

CROSS-REFERENCE TO RELATED APPLICATIONS

This application is a continuation of U.S. patent application Ser. No. 14/137,414, filed Dec. 20, 2013, now U.S. Pat. No. 9,121,926, which claims priority to and the benefit of U.S. Provisional Patent Application No. 61/745,518, filed Dec. 21, 2012, the entireties of which are hereby incorporated by reference.

TECHNICAL FIELD

The present disclosure relates generally to the field of medical devices and, more particularly, to control of the acquisition, processing, and display of medical imaging data within an intravascular ultrasound system.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS devices carry a transducer complex that includes an array of ultrasound transducers distributed around the circumference of the device connected to a set of transducer controllers. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the imaging system with a simple electrical cable and a standard detachable electrical connector.

Innovations in IVUS catheters have resulted in dramatic improvements in sensitivity and resolution, thereby enhancing the quality of diagnostic data obtained. As the sensing instruments improve, the onus is placed on the imaging system and the associated processing methods to keep pace. This has coincided with the development of multi-modality systems that collect and process medical data from a plurality of different imaging, treatment, diagnostic, and sensing tools including angiography, intravascular ultrasound (IVUS), forward-looking IVUS (FL-IVUS), fractional flow reserve (FFR) determination, a coronary flow reserve (CFR) determination, optical coherence tomography (OCT), transesophageal echocardiography, and image-guided therapy.

The increased data and processing power available allows for greater refinement of the IVUS processing techniques. However, such improvements may drive the algorithms and processes to become increasingly application specific. Each variant of the process may be better suited for different diagnostic situations. Furthermore, while the IVUS imaging process may be adjusted to suit the imaging environment, this fine-tuning often places the burden on the user to understand and apply the correct adjustments. Surgical time is expensive, and system features that are complicated and time consuming may see infrequent use. Thus, while existing imaging systems have proved useful, there remains a need for user interface improvements that allow the operator greater control over the system without overwhelming the operator with options.

SUMMARY

Embodiments of the present disclosure provide an enhanced system and method for providing an adaptive user interface for both dedicated imaging systems and multi-modality processing systems.

The systems and methods of the present disclosure provide a user interface for controlling an IVUS imaging system in the collection and processing of IVUS echo data utilizing an adaptive listing of task-based imaging mode options. To simplify the interface and reduce clutter, in some embodiments, the list is populated with the most relevant imaging mode options, while less relevant mode options are omitted. The user then selects an imaging mode from the presented list, and a set of operating parameters is generated that configures the IVUS system accordingly. This allows the user to configure the system quickly and accurately based on the task at hand and relieves the user of the burden of determining and applying individual operating parameters. In some embodiments, the operating parameters are fine-tuned according to other environmental information in order to improve the resulting IVUS image without further user prompting. This may also allow the system to perform dynamic adaptive refinement of operating parameters in response to changing conditions without further user attention. In this way, the systems and methods of the present disclosure provide extensive control over the IVUS imaging system in an intuitive and efficient manner. Of course, it is understood that these advantages are merely exemplary and that no particular advantage is required for any particular embodiment.

In some embodiments, a method for configuring a medical processing system is provided. The method comprises presenting a set of mode options to a user at a user display device. A mode selection, selected by the user, is received from the presented set of mode options. A set of operating parameters is determined based on the mode selection and at least one of a previous mode selection, a user preference, an operative course of a medical procedure, patient information, the first set of medical sensing data, a second set of medical sensing data, a status indicator, and a sensing device identifier. The medical processing system receives a first set of medical sensing data and processes the data according to the determined operating parameters.

In some embodiments, a method for presenting a user interface in a medical processing system is provided. The method comprises determining a set of mode options to be presented to a user. The set of mode options is determined based on at least one of a previous mode selection, a user preference, an operative course of a medical procedure, patient information, the set of medical sensing data, another set of medical sensing data, a status indicator, and a sensing device identifier, and the mode options define operating parameters associated with a sensing device. A mode selection, selected by the user, is received from the presented set of mode options. Based on the mode selection, a set of operating parameters associated with the sensing device are determined. The set of operating parameters is supplied to the medical processing system for use in processing a set of medical sensing data collected by the sensing device.

In some embodiments, an apparatus is provided. The apparatus comprises a non-transitory, computer-readable storage medium that stores a plurality of instructions for execution by at least one computer processor. The instructions include instructions for determining a set of mode options to be presented to a user, where each mode option of the set of mode options defines operating parameters associated with a sensing device. The instructions also include instructions for receives a mode selection, selected by the user, from the presented set of mode options and determining a set of operating parameters associated with the sensing device based on the mode selection. The instructions include further instructions for supplying the set of operating parameters to the medical processing system for use in processing a set of medical sensing data collected by the sensing device. In one such embodiment, the determining of the set of mode options is based on at least one of a previous mode selection, a user preference, an operative course of a medical procedure, patient information, the set of medical sensing data, another set of medical sensing data, a status indicator, and a sensing device identifier.

Additional aspects, features, and advantages of the present disclosure will become apparent from the following detailed description.

BRIEF DESCRIPTION OF THE DRAWINGS

FIGS. 1A, 1B, and 1C are schematic drawings depicting a medical system including an IVUS imaging system in various applications according to some embodiments of the present disclosure. In particular, FIG. 1A is illustrative of the medical system in a catheterization procedure according to some embodiments of the present disclosure. FIG. 1B is illustrative of the medical system in a cardiac catheterization procedure according to some embodiments of the present disclosure. FIG. 1C is illustrative of the medical system in a renal catheterization procedure according to some embodiments of the present disclosure.

DETAILED DESCRIPTION

Figure 1A:
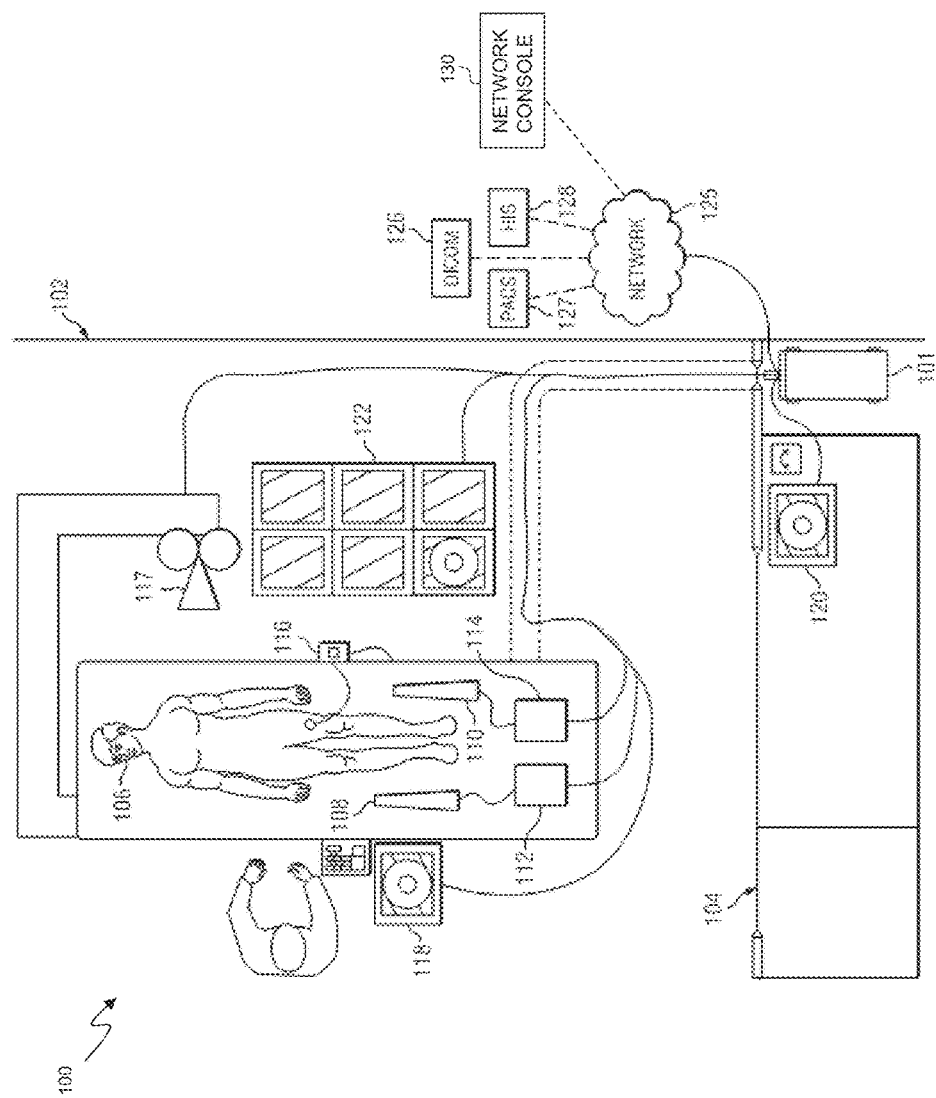

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIGS. 1A, 1B, and 1C are schematic drawings depicting a medical system including an IVUS imaging system in various applications according to some embodiments of the present disclosure. In general, the medical system 100 may be a single modality medical system, such as an IVUS system, and may also be a multi-modality medical system. In that regard, a multi-modality medical system provides for coherent integration and consolidation of multiple forms of acquisition and processing elements designed to be sensitive to a variety of methods used to acquire and interpret human biological physiology and morphological information and coordinate treatment of various conditions.

With reference to FIG. 1A, the imaging system 101 is an integrated device for the acquisition, control, interpretation, and display of one or more modalities of medical sensing data. Accordingly, in some embodiments, the imaging system 101 is a single modality imaging system, such as an IVUS imaging system, whereas, in some embodiments, the imaging system 101 is a multi-modality imaging system. In one embodiment, the imaging system 101 includes a computer system with the hardware and software to acquire, process, and display medical imaging data, but, in other embodiments, the imaging system 101 includes any other type of computing system operable to process medical data. In the embodiments in which the imaging system 101 includes a computer workstation, the system includes a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and/or a network communication device such as an Ethernet controller and/or wireless communication controller. In that regard, in some particular instances, the imaging system 101 is programmed to execute steps associated with the data acquisition and analysis described herein. Accordingly, it is understood that any steps related to data acquisition, data processing, instrument control, and/or other processing or control aspects of the present disclosure may be implemented by the imaging system 101 using corresponding instructions stored on or in a non-transitory computer readable medium accessible by the processing system. In some instances, the imaging system 101 is portable (e.g., handheld, on a rolling cart, etc.). Further, it is understood that in some instances imaging system 101 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

In the illustrated embodiment, the medical system 100 is deployed in a catheter lab 102 having a control room 104, with the imaging system 101 being located in the control room. In other embodiments, the imaging system 101 may be located elsewhere, such as in the catheter lab 102, in a centralized area in a medical facility, or at an off-site location accessible over a network. For example, the imaging system 101 may be a cloud-based resource. The catheter lab 102 includes a sterile field generally encompassing a procedure area, whereas the associated control room 104 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography (CT), intracardiac echocardiography (ICE), forward-looking ICE (FLICE), intravascular palpography, transesophageal ultrasound (TEE), thermography, magnetic resonance imaging (MRI), micro-magnetic resonance imaging (mMRI or μMRI), or any other medical sensing modalities known in the art. Further, the catheter lab and control room may be used to perform one or more treatment or therapy procedures on a patient such as radiofrequency ablation (RFA), cryotherapy, atherectomy or any other medical treatment procedure known in the art. For example, in catheter lab 102 a patient 106 may be undergoing a multi-modality procedure either as a single procedure or multiple procedures. In any case, the catheter lab 102 includes a plurality of medical instruments including medical sensing devices that collects medical sensing data in various different medical sensing modalities from the patient 106.

In the illustrated embodiment of FIG. 1A, instruments 108 and 110 are medical sensing devices that may be utilized by a clinician to acquire medical sensing data about the patient 106. In a particular instance, the device 108 collects medical sensing data in one modality, and the device 110 collects medical sensing data in a different modality. For instance, the instruments may each collect one of pressure, flow (velocity), images (including images obtained using ultrasound (e.g., IVUS), OCT, thermal, and/or other imaging techniques), temperature, and/or combinations thereof. In some embodiments, device 108 and 110 collect medical sensing data in different versions of similar modalities. For example, in one such embodiment, device 108 collects pressure data, and device 110 collects FFR (a pressure-based measurement) data. In another such embodiment, device 108 collects 20 MHz IVUS data, and device 110 collects 40 MHz IVUS data. Accordingly, the devices 108 and 110 may be any form of device, instrument, or probe sized and shaped to be positioned within a vessel, attached to an exterior of the patient, or scanned across a patient at a distance.

In the illustrated embodiment of FIG. 1A, instrument 108 is an IVUS catheter 108 that may include one or more sensors such as a phased-array transducer to collect IVUS sensing data. In some embodiments, the IVUS catheter 108 may be capable of multi-modality sensing such as IVUS and IVPA sensing. Further, in the illustrated embodiment, the instrument 110 is an OCT catheter 110 that may include one or more optical sensors configured to collect OCT sensing data. In some instances, an IVUS patient interface module (PIM) 112 and an OCT PIM 114, respectively, couple the IVUS catheter 108 and OCT catheter 110 to the imaging system 101. In particular, the IVUS PIM 112 and the OCT PIM 114 are operable to receive medical sensing data collected from the patient 106 by the IVUS catheter 108 and OCT catheter 110, respectively, and are operable to transmit the received data to the imaging system 101 in the control room 104. In one embodiment, the PIMs 112 and 114 include analog to digital (A/D) converters and transmit digital data to the imaging system 101. However, in other embodiments, the PIMs transmit analog data to the processing system. In one embodiment, the IVUS PIM 112 and OCT PIM 114 transmit the medical sensing data over a Peripheral Component Interconnect Express (PCIe) data bus connection, but, in other embodiments, they may transmit data over a USB connection, a Thunderbolt connection, a FireWire connection, an Ethernet connection, or some other high-speed data bus connection. In other instances, the PIMs may be connected to the imaging system 101 via wireless connections using IEEE 802.11 Wi-Fi standards, Ultra Wide-Band (UWB) standards, wireless FireWire, wireless USB, or another high-speed wireless networking standard.

Additionally, in the medical system 100, an electrocardiogram (ECG) device 116 is operable to transmit electrocardiogram signals or other hemodynamic data from patient 106 to the imaging system 101. In some embodiments, the imaging system 101 may be operable to synchronize data collected with the catheters 108 and 110 using ECG signals from the ECG 116. Further, an angiogram system 117 is operable to collect x-ray, computed tomography (CT), or magnetic resonance images (MRI) of the patient 106 and transmit them to the imaging system 101. In one embodiment, the angiogram system 117 is communicatively coupled to the processing system of the imaging system 101 through an adapter device. Such an adaptor device may transform data from a proprietary third-party format into a format usable by the imaging system 101. In some embodiments, the imaging system 101 is operable to co-register image data from angiogram system 117 (e.g., x-ray data, MRI data, CT data, etc.) with sensing data from the IVUS and OCT catheters 108 and 110. As one aspect of this, the co-registration may be performed to generate three-dimensional images with the sensing data.

A bedside controller 118 is also communicatively coupled to the imaging system 101 and provides user control of the particular medical modality (or modalities) being used to diagnose the patient 106. In the current embodiment, the bedside controller 118 is a touch screen controller that provides user controls and diagnostic images on a single surface. In alternative embodiments, however, the bedside controller 118 may include both a non-interactive display and separate controls such as physical buttons and/or a joystick. In the integrated medical system 100, the bedside controller 118 is operable to present workflow control options and patient image data in graphical user interfaces (GUIs). As will be described in greater detail in association with FIG. 2, in some embodiments, the bedside controller 118 includes a user interface (UI) framework service through which workflows associated with multiple modalities may execute. Thus, the bedside controller 118 may be capable displaying workflows and diagnostic images for multiple modalities allowing a clinician to control the acquisition of multi-modality medical sensing data with a single interface device.

A main controller 120 in the control room 104 is also communicatively coupled to the imaging system 101 and, as shown in FIG. 1A, is adjacent to catheter lab 102. In the current embodiment, the main controller 120 is similar to the bedside controller 118 in that it includes a touch screen and is operable to display a multitude of GUI-based workflows corresponding to different medical sensing modalities via a UI framework service executing thereon. In some embodiments, the main controller 120 is used to simultaneously carry out a different aspect of a procedure's workflow than the bedside controller 118. In alternative embodiments, the main controller 120 includes a non-interactive display and standalone controls such as a mouse and keyboard.

The medical system 100 further includes a boom display 122 communicatively coupled to the imaging system 101. The boom display 122 may include an array of monitors, each capable of displaying different information associated with a medical sensing procedure. For example, during an IVUS procedure, one monitor in the boom display 122 may display a tomographic view and one monitor may display a sagittal view.

Further, the multi-modality imaging system 101 is communicatively coupled to a data network 125. In the illustrated embodiment, the data network 125 is a TCP/IP-based local area network (LAN); however, in other embodiments, it may utilize a different protocol such as Synchronous Optical Networking (SONET), or may be a wide area network (WAN). The imaging system 101 may connect to various resources via the network 125. For example, the imaging system 101 may communicate with a Digital Imaging and Communications in Medicine (DICOM) system 126, a Picture Archiving and Communication System (PACS) 127, and a Hospital Information System (HIS) 128 through the network 125. Additionally, in some embodiments, a network console 130 may communicate with the multi-modality imaging system 101 via the network 125 to allow a doctor or other health professional to access the aspects of the medical system 100 remotely. For instance, a user of the network console 130 may access patient medical data such as diagnostic images collected by multi-modality imaging system 101, or, in some embodiments, may monitor or control one or more on-going procedures in the catheter lab 102 in real-time. The network console 130 may be any sort of computing device with a network connection such as a PC, laptop, smartphone, tablet computer, or other such device located inside or outside of a health care facility.

Additionally, in the illustrated embodiment, medical sensing tools in system 100 discussed above are shown as communicatively coupled to the imaging system 101 via a wired connection such as a standard copper link or a fiber optic link, but, in alternative embodiments, the tools may be connected to the imaging system 101 via wireless connections using IEEE 802.11 Wi-Fi standards, Ultra Wide-Band (UWB) standards, wireless FireWire, wireless USB, or another high-speed wireless networking standard.

One of ordinary skill in the art would recognize that the medical system 100 described above is simply an example embodiment of a system that is operable to collect diagnostic data associated with a plurality of medical modalities. In alternative embodiments, different and/or additional tools may be communicatively coupled to the imaging system 101 so as to contribute additional and/or different functionality to the medical system 100.

With reference now to FIG. 1B, an application of the medical system 100 includes a coronary catheterization procedure. The coronary catheterization procedure is merely one example of an application of the medical system 100. Whereas the coronary catheterization procedure is used to assess and/or treat disease states in the heart and related vessels, further exemplary catheterization procedures are used to assess and/or treat disease states in the kidneys and related vessels, in the carotid arteries and other vessels associated with the brain, in the peripheral vessels, and/or in other vascular structures. These catheterization procedures may be part of a treatment such as angioplasty, vascular stenting, valve repair, valve replacement, rotational atherectomy, intravascular ablation, peripheral artery disease (PAD) treatment, venous insufficiency treatment, and/or aneurysm intervention.

In an exemplary coronary catheterization procedure, a medical sensing instrument including a sensing catheter 150 is passed into a blood vessel of the heart 152 via the aorta 154. In some embodiments, a guide wire 156 is first advanced into the heart 152 through a large peripheral artery leading into the aorta 154. Once the guide wire 156 is properly located, a guide catheter 158 is advanced over the guide wire. The sensing catheter 150 is directed into position by traveling over the guide wire 156 and inside the guide catheter 158. In the illustrated embodiment, the distal tip of the sensing catheter 150 is advanced until it is positioned in the left coronary artery 160. The sensing catheter 150 is activated, and signals are passed between the catheter 150 and components of the system 100 such as the PIM 112 and/or the imaging system 101 of FIG. 1A. In the example of an IVUS sensing catheter 150, signals sent from the IVUS PIM 112 to one or more catheter transducers cause the transducer(s) to emit a specified ultrasonic waveform. Portions of the ultrasonic waveform are reflected by the surrounding vasculature and received by one or more receiving transducers of the catheter 150. The resulting echo signals are amplified for transmission to the IVUS PIM 112. In some instances, the PIM 112 amplifies the echo data, performs preliminary pre-processing of the echo data, and/or retransmits the echo data to the imaging system 101. The imaging system 101 aggregates and assembles the received echo data to create an image of the vasculature for display.

In some exemplary applications, the IVUS sensing catheter 150 is advanced beyond the area of the vascular structure to be imaged and pulled back as the transducers are operating, thereby exposing and imaging a longitudinal portion of the vessel. To ensure a constant velocity, a pullback mechanism is used in some applications. A typical withdraw velocity is 0.5 mm/s, although other rates are possible based on beam geometry, sample speed, and the processing power of the system (e.g., 1, 5, 10, 25, 50 mm/s). In some embodiments, the catheter 150 includes an inflatable balloon portion. As part of a treatment procedure, the device may be positioned adjacent to a stenosis (narrow segment) or an obstructing plaque within the vascular structure and inflated in an attempt to widen the restricted area.

With reference now to FIG. 1C, another application of the medical system 100 includes a renal catheterization procedure. In a renal catheterization procedure, the sensing catheter 170 is passed into a blood vessel of the kidneys 172 via the aorta. This may involve first advancing a guide wire and/or guide catheter and using the guide device(s) to control the advance of the sensing catheter 170. In the illustrated embodiment, the distal tip of the sensing catheter 170 is advanced until it is located in the right renal artery 174. Then, the sensing catheter 170 is activated and signals are passed between the catheter 170 and components of the system 100 such as the PIM 112 and/or the imaging system 101 of FIG. 1A. In the example of an IVUS sensing catheter 170, the signals contain echo data transmitted from the catheter 170 to the imaging system 101 by way of the IVUS PIM 112. The structures of the renal vasculature differ from those of the cardiac vasculature. Vessel diameters, tissue types, and other differences may mean that operating parameters suited to cardiac catheterization are less well suited to renal catheterization and vice versa. Furthermore, renal catheterization may target different structures, seeking to image the renal adventitia rather than arterial plaques, for example. For these reasons and more, the imaging system 101 may support different operating parameters for different applications such as cardiac and renal imaging. Likewise, the concept may be applied to any number of anatomical locations and tissue types.

Figure 2:
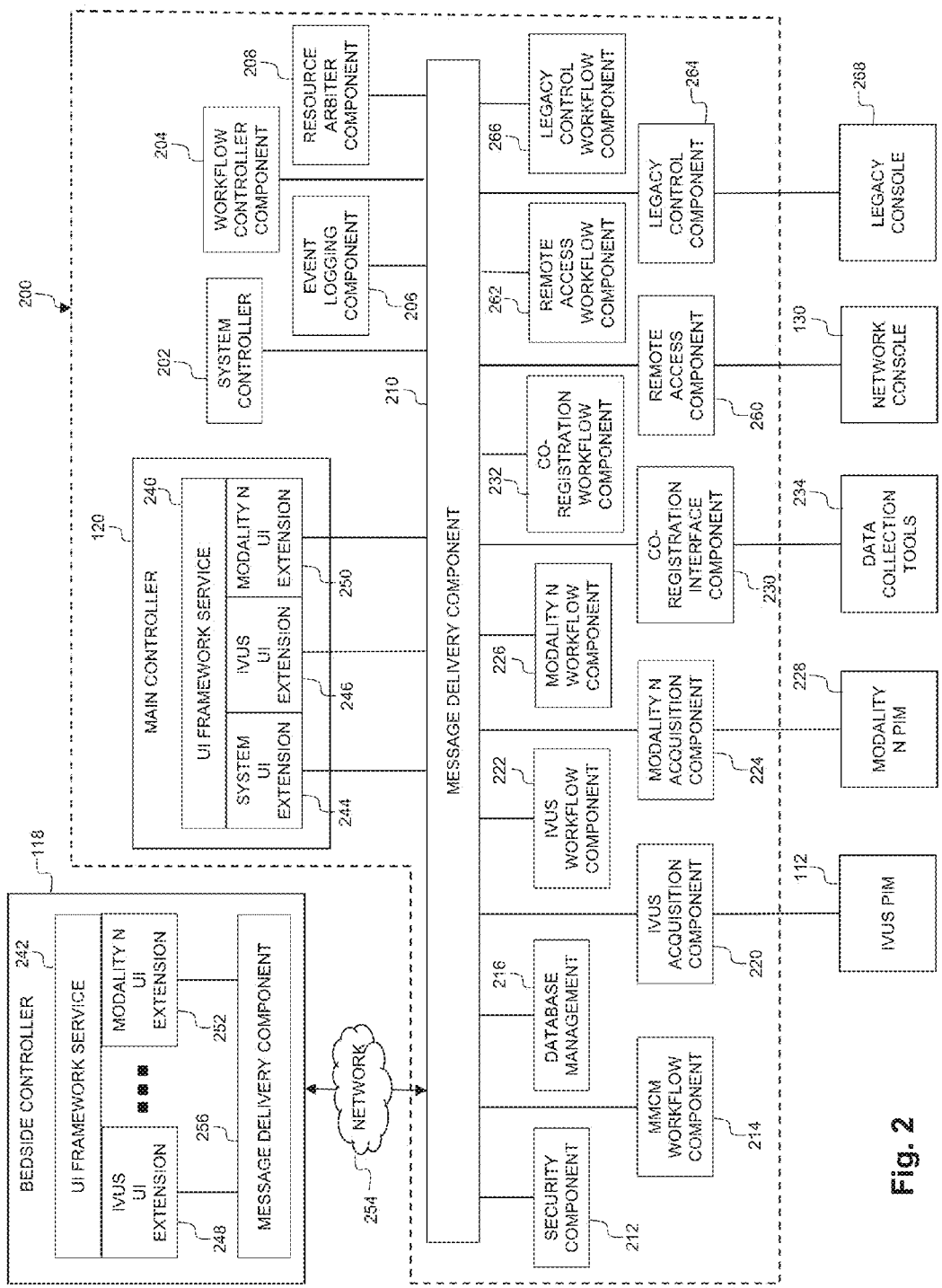
FIG. 2 is a functional block diagram of portions of the medical system of FIGS. 1A, 1B, and 1C, including a processing framework executing on some embodiments of the medical system.

With reference now to FIG. 2, illustrated is a functional block diagram of portions of the medical system 100 of FIGS. 1A, 1B, and 1C, including a processing framework 200 executing on some embodiments of the imaging system 101. The processing framework 200 includes various independent and dependent executable components that control the operation of the imaging system 101, including the acquisition, processing, and display of medical sensing data associated with one or more modalities. In general, the processing framework 200 of imaging system 101 is modular and extensible. That is, the framework 200 is comprised of independent software and/or hardware components (or extensions) respectively associated with different functions and medical sensing modalities. This modular design allows the framework to be extended to accommodate additional medical sensing modalities and functionality without impacting existing functionality or requiring changes to the underlying architecture. Further, an internal messaging system facilitates independent data communication between modules within the framework. In one instance, the processing framework 200 may be implemented as computer-executable instructions stored on a non-transitory computer-readable storage medium in the imaging system 101. In other instances, the processing framework 200 may be a combination of hardware and software modules executing within with the imaging system 101.

Generally, in the embodiment shown in FIG. 2, processing framework 200 includes a plurality of components that are configured to receive medical sensing data from one or more medical sensing devices, process the data, and output the data as diagnostic images via the main controller 120, the bedside controller 118, or other graphical display device. The framework 200 includes several system-level components that manage the core system functions of the imaging system 101 and also coordinate the plurality of modality-specific components. For instance, the framework 200 includes a system controller 202 that coordinates startup and shutdown of the plurality of executable components of the processing framework 200, including hardware and software modules related to acquisition and processing of patient diagnostic data. The system controller 202 is also configured to monitor the state of components executing within the framework 202, for instance, to determine if any components have unexpectedly stopped executing. In addition, the system controller 202 provides an interface through which other framework components may obtain system configuration and status information. Because the software framework 200 is modular, the system controller 202 is independent of the components within the framework that it manages so that errors and changes made to components do not affect the execution or structure of the system controller.

As mentioned above, the framework 200 is configured such that various extensions may be added and removed without system architecture changes. In certain embodiments, an extension executing within framework 200 may include a plurality of executable components that together implement the full functionality of the extension. In such embodiments, an extension may include an extension controller that is similar to the system controller 202 that is operable to startup, shutdown, and monitor the various executable components associated with the extension. For example, upon system startup, the system controller 202 may start an extension controller corresponding to a medical modality, and then the extension controller may, in turn, start the executable components associated with the modality. In one embodiment, extension controllers may be unallocated until system controller 202 associates them with a specific modality or other system task via parameters retrieved from a configuration mechanism, such as a configuration file.

The processing framework 200 further includes a workflow controller component 204 that is generally configured to govern the execution of the executable components of the framework 202 during medical sensing workflows. The workflow controller component 204 may govern workflows executed by the processing framework 200 in various different manners.

The processing framework 200 further includes an event logging component 206 that is configured to log messages received from various components of the processing framework. For instance, during system startup, the system controller 202 may send messages about the status of components being started to the event logging component 206 which, in turn, writes the messages to a log file in a standardized format. Additionally, the processing framework 200 includes a resource arbiter component 208 that is configured to manage the sharing of limited system resources between various executable components of the framework 202 during multi-modality medical sensing and/or treatment workflows. For example, during a multi-modality workflow, two or more components associated with different modalities within the processing framework 202 may be vying for the same system resource such as a graphical display on the main controller 120. The resource arbiter component 208 may coordinate sharing of limited system resources in various manners such as through a lock system, a queue system, or a hierarchical collision management system.

In one embodiment, the system controller 202, workflow controller component 204, event logging component 206, and resource arbiter component 208 may be implemented as processor-executable software stored on non-transitory, computer-readable storage media, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software. In certain embodiments in which executable components are implemented in FPGAs, the system controller 202 may be configured to alter the programmable logic within the FPGAs dynamically to implement various functionality needed at the time. As an aspect of this, the imaging system 101 may include one or more unassigned FPGAs that may be allocated by the system controller during system startup. For instance, if upon startup of the imaging system 101, the system controller detects an OCT PIM and catheter coupled thereto, the system controller or an extension controller associated with OCT functionality may dynamically transform the programmable logic within one of the unassigned FPGAs such that it includes functionality to receive and/or process OCT medical data.

To facilitate intersystem communication between different hardware and software components in the multi-modality imaging system 101, the processing framework 200 further includes a message delivery component 210. In one embodiment, the message delivery component 210 is configured to receive messages from components within the framework 202, determine the intended target of the messages, and deliver the messages in timely manner (i.e., the message delivery component is an active participant in the delivery of messages). In such an embodiment, message metadata may be generated by the sending component that includes destination information, payload data (e.g., modality type, patient data, etc.), priority information, timing information, or other such information. In another embodiment, message delivery component 210 may be configured to receive messages from components within the framework 202, temporarily store the messages, and make the messages available for retrieval by other components within the framework (i.e., the message delivery component is a passive queue). In any case, the message delivery component 210 facilitates communication between executable components in the framework 200. For instance, the system controller 202 may utilize the message delivery component 210 to inquire into the status of components starting up during a system startup sequence, and then, upon the receiving status information, utilize the message delivery component to transmit the status information to the event logging component 206 so that it may be written to a log file. Similarly, the resource arbiter component 208 may utilize the message delivery component 210 to pass a resource token between components requesting access to limited resources.

In one example embodiment in which the message delivery component 210 is a passive queue, components in the framework 200 may packetize incoming medical sensing data into messages and then transmit the messages to a queue on the message delivery component where they may be retrieved by other components such as image data processing components. Further, in some embodiments, the message delivery component 210 is operable to make received messages available in a First-In-First-Out (FIFO) manner, wherein messages that arrive on the queue first will be removed from the queue first. In alternative embodiments, the message delivery component 210 may make messages available in a different manner for instance by a priority value stored in a message header. In one embodiment, the message delivery component 210 is implemented in random-access memory (RAM) in the imaging system 101, but, in other embodiments, it may be implemented in non-volatile RAM (NVRAM), secondary storage (e.g., magnetic hard drives, flash memory, etc.), or network-based storage. Further, in one embodiment, messages stored on the message delivery component 210 may be accessed by software and hardware modules in imaging system 101 using Direct Memory Access (DMA).

The processing framework 202 may include a number of additional system components that provide core system functionality including a security component 212, a multi-modality case management (MMCM) component 214, and a database management component 216. In certain embodiments, the security component 212 is configured to provide various security services to the overall processing framework and to individual components. For example, components implementing an IVUS data acquisition workflow may utilize encryption application programming interfaces (APIs) exposed by the security component 212 to encrypt IVUS data before it is transmitted over a network connection. Further, the security component 212 may provide other security services, such as system-level authentication and authorization services to restrict access to the processing framework to credentialed users and also to prevent the execution of untrusted components within the extensible framework. The multi-modality case management (MMCM) component 214 is configured to coordinate and consolidate diagnostic data associated with a plurality of medical modalities into a unified patient record that may be more easily managed. Such a unified patient record may be more efficiently stored in a database and may be more amenable to data archival and retrieval. In that regard, the database management component 216 is configured to present transparent database services to the other components in the framework 200 such that database connection and management details are hidden from the other components. For example, in certain embodiments, the database management component 216 may expose an API that includes database storage and retrieval functionality to components of the framework 200. In other words, a medical sensing workflow component may be able to transmit diagnostic data to a local and/or remote database such as a DICOM or PACS server via the database component without being aware of database connection details. In other embodiments, the database management component 216 may be operable to perform additional and/or different database services such as data formatting services that prepare diagnostic data for database archival.

As mentioned above, the processing framework 200 of the imaging system 101 is operable to receive and process medical data associated with one or a plurality of modalities. In multi-modal embodiments, the processing framework 200 includes a plurality of modular acquisition components and workflow components that are respectively associated with different medical sensing and diagnostic modalities. For instance, as shown in the illustrated embodiment of FIG. 2, the processing framework 200 includes an IVUS acquisition component 220 and an IVUS workflow component 222 that are respectively configured to receive and process IVUS medical sensing data from the IVUS PIM 112. In accordance with the modular and extensible nature of the processing framework 200, any number of additional acquisition and workflow components may be independently added to the framework as denoted by the modality "N" acquisition component 224 and the modality "N" workflow component 226 that acquire and process data from a modality "N" PIM 228. For example, in certain embodiments, the imaging system 101 may be communicatively coupled to the OCT PIM 114, the ECG system 116, a fractional flow reserve (FFR) PIM, an FL-IVUS PIM, and an ICE PIM. In other embodiments, additional and/or different medical sensing, treatment, or diagnostic devices may be coupled to the imaging system 101 via additional and/or different data communication connections known in the art. In such a scenario, in addition to the IVUS acquisition module 220, the processing framework 200 may include an FFR acquisition component to receive FFR data from an FFR PIM, an FL-IVUS acquisition component to receive FL-IVUS data from an FL-IVUS PIM, an ICE acquisition component to receive ICE data from an ICE PIM, and an OCT acquisition component is operable to receive OCT data from an OCT PIM. In this context, medical data communicated between the executable components of the processing framework 200 and the communicatively coupled medical devices (e.g., PIMs, catheters, etc.) may include data collected by sensors, control signals, power levels, device feedback, and other medical data related to a sensing, treatment, or diagnostic procedure. Further, in certain embodiments, patient treatment devices may be communicatively coupled to the imaging system 101 such as devices associated with radiofrequency ablation (RFA), cryotherapy, or atherectomy and any PIMs or other control equipment associated with such treatment procedures. In such an embodiment, the modality "N" acquisition component 224 and the modality "N" workflow component 226 may be configured to communicate with and control the treatment devices such as by relaying control signals, relaying power levels, receiving device feedback, and receiving data collected by sensors disposed on the treatment devices.

In one embodiment, once the acquisition components 220 and 224 have received data from connected medical sensing devices, the components packetize the data into messages to facilitate intersystem communication. Specifically, the components may be operable to create a plurality of messages from an incoming digital data stream, where each message contains a portion of the digitized medical sensing data and a header. The message header contains metadata associated with the medical sensing data contained within the message. Further, in some embodiments, the acquisition components 220 and 224 may be operable to manipulate the digitized medical sensing data in some way before it is transmitted to other portions of the framework 200. For example, the acquisition components may compress the sensing data to make intersystem communication more efficient, or normalize, scale or otherwise filter the data to aid later processing of the data. In some embodiments, this manipulation may be modality-specific. For example, the IVUS acquisition component 220 may identify and discard redundant IVUS data before it is passed on to save processing time in subsequent steps. The acquisition components 220 and 224 may additionally perform a number of tasks related to the acquisition of data including responding to interrupts generated by data buses (e.g., PCIe, USB), detecting which medical sensing devices are connected to imaging system 101, retrieving information about connected medical sensing devices, storing sensing device-specific data, and allocating resources to the data buses. As mentioned above, the data acquisition components are independent from each other and may be installed or removed without disrupting data acquisition by other components. Additionally, acquisition components are independent of underlying data bus software layers (for example, through the use of APIs) and thus may be created by third parties to facilitate acquisition of data from third party medical sensing devices.

The workflow components of the processing framework, such as the IVUS workflow component 222, receive unprocessed medical sensing and/or diagnostic data from respective acquisition components via the message delivery component 210. In general, the workflow components are configured to control the acquisition of medical sensing data such as by starting and stopping data collection at calculated times, displaying acquired and processed patient data, and facilitating the analysis of acquired patient data by a clinician. As an aspect of this, the workflow components are operable to transform unprocessed medical data gathered from a patient into diagnostic images or other data formats that enable a clinician to evaluate a patient's condition. For example, an IVUS workflow component 222 may interpret IVUS data received from the IVUS PIM 112 and convert the data into human-readable IVUS images. In one embodiment, a software stack within the framework may expose a set of APIs with which the workflow component 222 and other workflow components in the framework may call to access system resources such as the computational resources, the message delivery component 210, and communication resources. After processing acquired data, the modality-centric workflow components may transmit one or messages containing the processed data to other components within the framework 200 via the message delivery component 210. In some embodiments, before sending such messages, the components may insert a flag in the header indicating that the message contains processed data. Additionally, in some embodiments, after processing medical sensing data, the components may utilize the database management component 216 to transmit the processed data to archival systems such as a locally attached mass storage device or the network-based PACS server 127. In accordance with the modular architecture of the processing framework 200, the workflow components 222 and 226 are independent of each other and may be installed or removed without disrupting other components, and may be written by third parties. Further, due to their independence, they may be are operable to process signaling and imaging data from multiple medical sensing devices concurrently.

The processing framework 200 additionally includes a co-registration interface component 230 and a co-registration workflow component 232 that are configured to acquire and process data from any number of data collection tools 234 and co-register the acquired data with data acquired by one of the other acquisition components within the framework. In more detail, the co-registration interface component 230 may be operable to communicatively interface with medical data acquisition tools associated with any number of modalities, such as the ECG device 116 or the angiography system 117 of FIG. 1A. In certain embodiments, the interface component 230 may be operable to standardize and/or transform incoming modality data such that it may be co-registered with other sensing data acquired by the imaging system 101. As medical data is being acquired by the co-registration interface component 230, the co-registration workflow component 232 is configured to facilitate the co-registration of data from different modalities such as by spatially or temporally synchronizing data collection among medical sensing devices, aligning two or more acquired data sets based on spatial or temporal registration markers, and generating co-registered diagnostic images or other human-readable data that enable a clinician to evaluate a patient's condition. Further, in other embodiments, the co-registration workflow component 232 may be operable to spatially co-register catheter-gathered data in a two-dimensional (2-D) or three-dimensional (3-D) space using previously-generated 2-D images or 3-D models. For example, a catheter-based sensing tool may include fiducials that are tracked to generate position data during a sensing procedure, and the co-registration workflow component 232 may register this position data against previously acquired MRI data. Still further, the co-registration workflow component 232 may facilitate co-registration of multi-modality data acquired by native acquisition components within the framework 200 such as the IVUS acquisition component 220 and modality "N" acquisition component 224. Additionally, in some embodiments, a real-time clock may be integrated into the co-registration workflow component 232. U.S. Pat. No. 8,797,155, entitled "DISTRIBUTED MEDICAL SENSING SYSTEM AND METHOD", discloses temporally synchronizing medical sensing data collection in more detail and is hereby incorporated by reference in its entirety.

As discussed above in association with FIG. 1A, a clinician utilizing the imaging system 101 may control workflows and view diagnostic images through the main controller 120 and the bedside controller 118. The main controller 120 and the bedside controller 118 respectively include user interface (UI) framework services 240 and 242 that support a plurality of user interface (UI) extensions (or components). In general, the UI extensions supported by the UI framework services 240 and 242 respectively correspond to medical sensing modalities and are operable to render a user interface for control of the associated acquisition workflow and display of processed sensing data. Similar to the processing framework 200, the UI frameworks 240 and 242 are extensible in that they support UI extensions that are independent of one another. That is, its modular design allows the UI frameworks 240 and 242 to be extended to accommodate additional medical sensing modality user interfaces without impacting existing user interfaces or requiring changes to the underlying UI architectures. In the illustrated embodiment, the main controller 120 includes a system UI extension 244 that renders a user interface containing core system controls and configuration options. For example, a clinician may startup, shutdown or otherwise manage the imaging system 101 using the user interface rendered by the system UI extension 244. In one embodiment, the components of the main controller 120 may be considered part of the processing framework 200. The IVUS UI extensions 246 and 248 render user interfaces for the main controller 120 and bedside controller 118, respectively. For example, the IVUS UI extensions 246 and 248 may render and display the touch screen buttons used to control an IVUS workflow and also render and display the IVUS diagnostic images created by the IVUS workflow component 222. Similarly, the modality "N" UI extensions 250 and 252 render controls and images associated with a modality "N" workflow.

In one embodiment, the UI framework services 240 and 242 may expose APIs with which the UI extensions may call to access system resources such as a look-and-feel toolbox and error handling resources. Look-and-feel toolbox APIs enable the UI extensions to present a standardized user interface with common buttons, parallel workflow formats, and data presentation schemes for different modality workflows. In this manner, clinicians may more easily transition between acquisition modalities without additional user interface training. Further, co-registration UI extensions may present and/or combine processed image or signaling data from multiple modalities. For instance, a UI extension may display an electrocardiogram (ECG) wave adjacent to IVUS imaging data or may display an IVUS image overlaid with borders that were previously drawn on an OCT image. Further, in some embodiments, the UI framework services 240 and 242 may include a multi-tasking framework to coordinate concurrently executing UI extensions. For instance, in the event the imaging system 101 is simultaneously acquiring data associated with more than one modality, the UI framework services 240 and 242 may present the user with a modality selector screen on which a desired user interface may be selected.

The UI framework service 240 communicates with the components of the processing framework 200 via the message delivery component 210. As shown in the illustrated embodiment of FIG. 2, the bedside controller 118 may be communicatively coupled to the processing framework 200 via a network connection 254. The network connection 254 may be any type of wired of wireless network connection such as an Ethernet connection or IEEE 802.11 Wi-Fi connection. Alternatively, one or both of the main and bedside controllers 120 and 118 may communicate with the processing framework 200 via a local bus connection such as a (PCIe) data bus connection, a USB connection, a Thunderbolt connection, a FireWire connection, or some other high-speed data bus connection. Further, in the illustrated embodiment of FIG. 2, the bedside controller includes a message delivery component 256 that is configured to facilitate message-based communication between the UI extensions in the bedside controller 118 and the components in the processing framework 200. In certain embodiments, the message delivery component 256 may extract diagnostic image data from network communication packets as they arrive over the network connection 254.

The processing framework 200 includes additional components that allow a clinician to access and/or control workflows executing in the multi-modality imaging system 101. For example, the framework 200 includes a remote access component 260 that communicatively couples the network console 130 (FIG. 1A) to the processing framework 200. In one embodiment, the remote access component 260 is operable to export control functionality of the imaging system 101 to the network console 130, so that the network console may present workflow control functions in its user interface. In certain embodiments, the remote access component 260 may receive workflow commands from the network console 130 and forward them to a remote access workflow component 262. The remote access workflow component 262 may dictate the set of commands and diagnostic data to which a remote user may access through the network console 130. Further, the legacy control component 264 and legacy control workflow component 266 provide some level of access to modality workflow control and data to users of legacy consoles 268 (e.g. button consoles, mice, keyboards, standalone monitors).

In one embodiment, the core system components of the processing framework 200 and the additional components such as the modality-related components may be implemented as processor-executable software stored on non-transitory, computer-readable storage media, but in alternative embodiments, these components may be implemented as hardware components such as special purpose microprocessors, Field Programmable Gate Arrays (FPGAs), microcontrollers, graphics processing units (GPU), digital signal processors (DSP). Alternatively, the components of the processing framework may be implemented as a combination of hardware and software.

One of ordinary skill in the art will recognize that the processing framework 200 of FIG. 2 is simply an example embodiment and, in alternative embodiments, the framework may include different and/or additional components configured to carry out various medical sensing workflows. For instance, the processing framework 200 may further include executable components configured for the evaluation of a stenosis of a human blood vessel or configured to facilitate control of computer-assisted surgery or remotely-controlled surgery.

Figure 3:
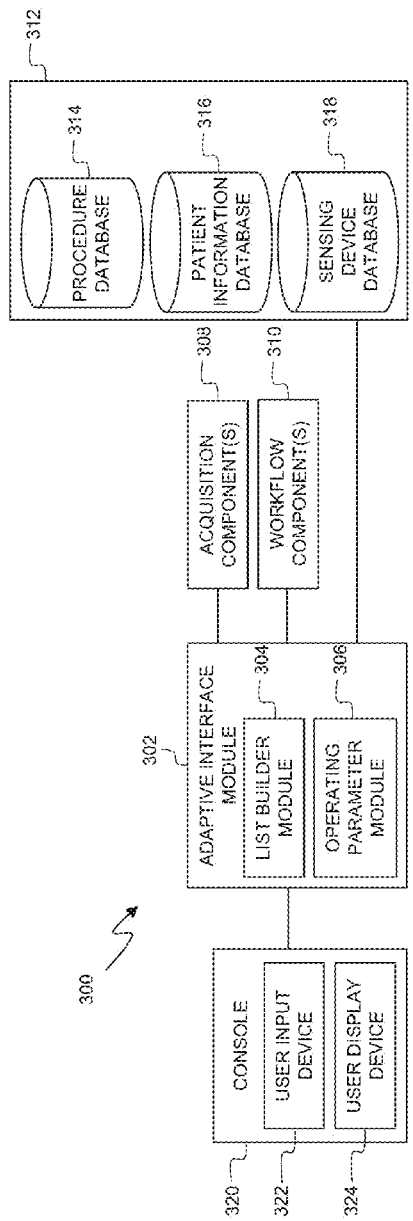
FIG. 3 is a functional block diagram of portions of the medical system of FIGS. 1A, 1B, and 1C, including a user interface component for providing an adaptive user interface for the control of the acquisition, processing, and display of medical imaging data according to some embodiments of the present disclosure.

Referring now to FIG. 3 illustrated is a functional block diagram of portions of the medical system of FIGS. 1A, 1B, and 1C, including a user interface component 300 for providing an adaptive user interface for the control of the acquisition, processing, and display of medical imaging data according to some embodiments of the medical system 100. The user interface component 300 allows users to adjust operating characteristics of the system 100 by selecting task-based imaging modes from a list of mode options without delving into the minutia of the underlying control parameters corresponding to each imaging mode. Exemplary imaging modes will be described in further detail below, but, in brief, imaging modes may by characterized by target structure, vasculature segment, vasculature type, tissue type, gross anatomical location, surgical procedure, focal distance, and/or other suitable criteria. The user selects an imaging mode from the presented list, and the interface component 300 optimizes a behavior of the sensing device and/or a processing component of the medical system 100 accordingly. This allows the user to reconfigure the system quickly and accurately based on the task at hand and relieves the user of the burden of determining and applying individual operating parameters corresponding to the task. The user interface component 300 may also perform dynamic adaptive enhancement of operating parameters in response to changing conditions without further user attention.

The user interface component 300 includes an adaptive interface module 302 comprising a list builder module 304 and an operating parameter module 306. In various embodiments, the adaptive interface module 302 is communicably coupled to one or more acquisition components 308 such as an IVUS acquisition component (e.g., IVUS acquisition component 220 of FIG. 2), an FL-IVUS acquisition component, an OCT acquisition component, and/or other modality acquisition components. The interface module 302 may also be communicably coupled to one or more workflow components 310, including an IVUS workflow component (e.g., IVUS workflow component 222 of FIG. 2), an FL-IVUS workflow component, an OCT workflow component, and/or other modality workflow components. In some embodiments, the interface module 302 is communicatively coupled to one or more databases 312 such as a procedure database 314, a patient information database 316, a sensing device database 316, and/or other databases. The interface module 302 is also communicatively coupled to a user console 320, which may include a user input device 322 and a user display device 324. Examples of suitable user input devices 322 include, but are in no way limited to, keyboards, keypads, mice, trackballs, digital pens, touch-based interfaces, gesture-based interfaces, verbal and speech-recognition interfaces, adaptive interfaces, cameras, motion-sensing interfaces, and/or other user input devices known to one of skill in the art.

Portions of the user interface component 300 may be implemented, in whole or in part, as processor-executable software stored on non-transitory, computer-readable storage media and/or as hardware components such as special purpose microprocessors, FPGAs, microcontrollers, graphics processing units, and DSPs. In some embodiments, portions of the user interface component 300 are incorporated into components of the processing system 100 described with reference to FIGS. 1A, 1B, and 1C and FIG. 2. For example, in some such embodiments, user console 320 is a component of a bedside controller 118, a main controller 120, a boom display 122, and/or a network console 130 described with reference to FIG. 1A. As a further example, in some such embodiments, the adaptive interface module 302 is incorporated into a UI framework service 240 of a main controller 120, a UI framework service 242 of a bedside controller 118, and/or a UI extension such as IVUS UI extension 246 or IVUS UI extension 248 as described with reference to FIG. 2. In other embodiments, the interface module 302 is a separate and distinct component of the multi-modality processing system 100.

The adaptive interface module 302 presents a set of user-selectable imaging mode options assembled in a list by the list builder module 304 to the operator via the user display device 324. Exemplary mode options may by characterized by target structure, vasculature segment, vasculature type, tissue type, gross anatomical location, procedure, focal distance, and/or other suitable criteria. For example, the user interface may present imaging mode options corresponding to target structures of interest (e.g., coronary plaque, carotid plaque, peripheral plaque, coronary adventitia, renal adventitia, stent, etc.). In a further example, the list contains mode options corresponding to segments of the vasculature (e.g., left anterior descending artery, left circumflex artery, left main coronary artery, right coronary artery, etc.). In another example, the interface component 300 presents the user with mode options corresponding to vasculature type (e.g., coronary vasculature, renal vasculature, peripheral vasculature, bifurcation, etc.). In another example, the list contains mode options corresponding to surgical procedures (e.g., coronary imaging, balloon angioplasty, stent placement, plaque ablation, renal tissue ablation, etc.). Additionally mode options may be characterized by multiple criteria such as focal distance and target structure or vasculature segment and current surgical procedure. Accordingly, the list of imaging mode options may include imaging modes corresponding to any one or any number of suitable criteria, including any combinations of those described above.

In some embodiments, the list builder module 304 collects and analyzes information pertaining to the current imaging environment to determine the relevant imaging mode options. For example, when an IVUS catheter is located within a renal artery, renal imaging modes may be more relevant than cardiac imaging modes. As another example, during a stenting procedure of the left coronary artery, imaging modes corresponding to right coronary vasculature segments may be less relevant than those corresponding to left coronary vasculature segments. Therefore, the list builder module 304 adapts the list of imaging mode options to include relevant mode options and exclude less relevant mode options based on the operating environment information. In various embodiments, this environmental data includes previous user mode selections, user preferences, the operative course of a procedure, patient information, correlated medical data from other modalities, status indicators, sensing device identifiers, and/or other data that describes the operating environment. By displaying only the most relevant imaging modes, the user interface component 300 presents a succinct, streamlined interface with improved clarity and readability.

Various exemplary embodiments will now be described. Of course, these embodiments are merely exemplary; other types and uses of environmental data are both contemplated and provided for. In some embodiments, the list builder module 304 receives a previous user mode selection. The previous selection may be received from a storage component of the list builder module 304, from another component of the system 100, from a remote storage resource accessible by the system 100, for example, a network storage device, and/or from another storage device. In some embodiments, the previous selection is used by the list builder module 304 to determine the frequency that particular imaging modes are selected. Frequently selected modes may be weighted in favor of being included in the list, while infrequently selected modes may be weighted in favor of being excluded. In some embodiments, the previous mode selection is used by the list builder module 304 to determine the frequency with which a particular mode selection follows another mode selection. For example, the list builder module may determine common orders or flows of user-selected imaging modes. Similarly, in some embodiments, the list builder module 304 receives a user preference from a storage component of the list builder module 304, from another component of the system 100, from a remote storage resource accessible by the system 100, for example, a network storage device, and/or from another storage device. The list builder module 304 uses the user preference to determine relevant mode options. In various such embodiments, the user preference allows operators to define favorite imaging modes, to expand the system 100 by providing new imaging modes (e.g., by setting custom parameters associated with a new imaging mode), and/or to adjust existing imaging modes.

In some embodiments, the list builder module 304 receives a medical procedure flow from a procedure database 314 and uses the procedure flow to determine relevant mode options. For example, a stent-placement procedure may have a pre-stent-deployment imaging mode and post-stent-deployment imaging mode. The procedure flow may correspond to a customary course of an operative procedure as well as variations, deviations, and related procedures. In some embodiments, the procedure flow specifies imaging modes to be included in the list and/or specifies imaging modes to be excluded from the list. In some embodiments, the procedure flow designates variations, deviations, and related procedures that are only selectable after a warning is displayed and/or additional confirmation is received. The procedure flow may also specify how imaging modes progress from one to the next. For example, a flow may specify that a pre-stent-deployment imaging mode is typically followed by a post-stent-deployment imaging mode. Accordingly, in some embodiments, the list builder module 304 utilizes the procedure flow and a previous user response to predict subsequent imaging modes. The predicted imaging modes are then included in the list to be presented.

In some embodiments, the list builder module 304 receives patient data from a patient information database 316 and utilizes the patient data to determine the mode options to present. Exemplary patient data includes the patient's name, past medical history, vital statistics, and/or the procedure(s) scheduled for the patient.

In some embodiments, the list builder module 304 receives medical sensing data corresponding to a modality of the system 100 and utilizes the medical data to determine the mode options to present. The medical data may be the current sensing data or any other suitable medical data, may correspond to the current modality or any other suitable modality, and may be in an unprocessed or processed form. In that regard, in an exemplary embodiment, the list builder module 304 receives unprocessed medical imaging data, such as raw IVUS, pressure, or flow data, from a modality acquisition component 308 (e.g., an IVUS acquisition component, an FL-IVUS acquisition component, another modality acquisition component, etc.). In another such embodiment, the list builder module 304 receives processed medical imaging data, such as focused IVUS data or processed pressure or flow data, from a modality workflow component 310 (e.g., an IVUS workflow component, an FL-IVUS workflow component, a pressure workflow component, a flow workflow component, another modality workflow component, etc.).

The received sensing data may be used to refine the list of imaging modes to be presented. For example, the list builder module 304 may receive IVUS sensing data that includes a hot spot caused by a strong ultrasonic reflector such as a coronary stent. In various such embodiments, based on this sensing data, the module 304 lists an imaging mode option to colorize the device within the IVUS image, lists an imaging mode option to correct the overall contrast to account for the hot spot, and/or lists an imaging mode option to measure and display blood flow around the stent, for example, to detect possible stent malapposition. In a further example, the list builder module 304 receives IVUS imaging data, utilized a border-detection process on the imaging data to determine the size of the surrounding vasculature and presents imaging modes having focal distances sized accordingly. In a further example, the list builder module uses a border-detection process to determine a segment of vasculature corresponding to the IVUS data and presents imaging modes configured to the particular vasculature segment. In a further example, the list builder module 304 identifies a plaque structure from IVUS imaging data, and applies an algorithm to the imaging data to estimate a degree of calcification. The list builder module 304 presents imaging modes configured to produce an optimal image based on the type of plaque. In yet a further example, the list builder module 304 analyzes the received sensing data and flags particular imaging modes as selectable only after a warning is displayed and/or additional confirmation is received.

In an example of a multi-modality application, the list builder module 304 receives IVUS imaging data and radiographic data indicating the location of the IVUS catheter producing the imaging data. The IVUS catheter may include radiographic fiducials that exhibit an identifiable radiographic signature to facilitating the locating of the catheter. From the radiographic data, the list builder module 304 determines an anatomical location of the IVUS catheter within the body and populates the list of presented modes based on structures located near the catheter. In this way, the list builder module 304 utilizes the radiographic data to select appropriate imaging modes to present.

In some embodiments, the list builder module 304 receives a status indicator from a component of the system 100 and utilizes the status indicator to determine the mode options to present. Exemplary status indicators correspond to system states, system readiness, readiness of an attached device, device identifiers and/or other suitable indicators. For example, in an embodiment, a status indicator is received that signifies that the system 100 supports tissue characterization and is in communication with a tissue characterization database. The list builder module 304 may then present a number of tissue characterization mode options for the user to select from. In another exemplary embodiment, a status indicator including a sensing device identifier is received by the module 304. The sensing device identifier may contain the make and model of a sensing device coupled to the system 100. As certain sensing devices support certain imaging modes and data collection, the list of mode options may be populated accordingly. In some such embodiments, the list builder module 304 queries the sensing device database 316 using the device identifier to determine the supported imaging modes. In yet another exemplary embodiment, the status indicator signifies that a second sensing device in a second modality is active and ready. Based on this status indicator, list builder module 304 lists user mode options that collect multi-modality data and that enhance data sets using the different modalities. For example, an IVUS dataset may be cross-correlated and enhanced using a set of pressure or flow measurements.

Thus, in various embodiments, the list builder module 304 receives environmental data such as previous user-selected imaging modes, user preferences, the operative course of a procedure, patient information, correlated medical data from the current modality and other modalities, status indicators, sensing device identifiers, and/or other data that describes the imaging environment and assembles a list of relevant user-selectable imaging mode options. These examples are non-limiting and are offered only for clarity.

The adaptive interface module 302 receives the list of imaging mode options from the list builder module 304 and presents the list to the user via the console 320. The adaptive interface module 302 then receives a mode selection via the user input device 322 of the console 320. In some embodiments, the user may supply an alternative mode not included in the list either in addition to or as a substitute for selecting a mode option from the list. For example, the user may enter operating parameters and/or a mode name associated with a new mode using the user input device 322.

Based in part on the user's mode selection, the operating parameter module 306 of the adaptive interface module 302 determines a set of operating parameters for the system 100. Operating parameters for IVUS imaging modes may include catheter parameters such as ultrasonic waveform parameters, emitter power, amplification, and emitter/receiver patterns. In addition or in the alternative, the operating parameters include processing parameters such as gain, sensitivity, sampling rates, grayscale or pseudo-color conversion factors, apodization coefficients, weighting coefficients, log compression curves, time-gain compensation (TGC) factors, time-of-flight adjustments, signal filtering parameters, signal filter types (e.g., IIR, FIR, median, mean, diffusion-weighted, etc.). Any or all of the operating parameters may be provided to the user to view or hidden to remove screen clutter, and the operating parameters may be co-registered with the sensing data.

In some exemplary embodiments, the operating parameters determine gain or amplification factors for one or more of a sensing device (such as an IVUS catheter), a PIM coupled to the sensing device, an imaging system 101 coupled to the PIM, and/or another component of the medical system 100. In some exemplary embodiments, the operating parameters determine a sampling rate or sampling pattern by which an analog signal such as an IVUS ultrasound data is digitized.

Some IVUS images consist of a bitmap image where a pixel color at a location corresponds to the intensity of an ultrasound echo produced by an anatomical structure at a corresponding location. In a grayscale image, pixels with higher luminance may correspond to structures with greater reflectivity. Accordingly, in some embodiments, the parameter module 306 may determine operating parameters that affect the conversion of echo strength to a grayscale value. In a pseudo-color image, pixels may be assigned a color corresponding to echo strength. Accordingly, in some embodiments, the parameter module 306 may determine operating parameters that affect the conversion of echo strength to a pseudo-color value.

In some embodiments, an operating parameter set by the parameter module 306 enables a fluid flow analysis such as ChromaFlo® (a trademark of Volcano Corporation). U.S. Pat. No. 5,921,931, entitled "METHOD AND APPARATUS FOR CREATING A COLOR BLOOD FLOW IMAGE BASED UPON ULTRASONIC ECHO SIGNALS RECEIVED BY AN INTRAVASCULAR ULTRASOUND IMAGING PROBE," U.S. Patent Application Publication No. 2014/0350404, entitled "METHOD FOR VISUALIZING BLOOD AND BLOOD-LIKELIHOOD IN VASCULAR IMAGES," and U.S. Patent Application Publication No. 2013/0303907, entitled "DEVICE AND SYSTEM FOR IMAGING AND BLOOD FLOW VELOCITY MEASUREMENT," disclose fluid flow analysis in greater detail and are hereby incorporated by reference in their entirety.

In some embodiments, an operating parameter set by the parameter module 306 may enable a tissue characterization process such as Virtual Histology™ (a trademark of Volcano Corporation). U.S. Pat. No. 6,200,268 entitled "VASCULAR PLAQUE CHARACTERIZATION," U.S. Pat. No. 6,381,350 entitled "INTRAVASCULAR ULTRASONIC ANALYSIS USING ACTIVE CONTOUR METHOD AND SYSTEM," U.S. Pat. No. 7,074,188, entitled "SYSTEM AND METHOD OF CHARACTERIZING VASCULAR TISSUE, U.S. Pat. No. 7,175,597, entitled "NON-INVASIVE TISSUE CHARACTERIZATION SYSTEM AND METHOD," and U.S. Pat. No. 7,988,633, entitled "APPARATUS AND METHOD FOR USE OF RFID CATHETER INTELLIGENCE," disclose tissue characterization based on IVUS echo signals in greater detail and are hereby incorporated by reference in their entirety.

In some embodiments, the parameter module 306 determines operating parameters that include a focusing parameter such as an apodization coefficient, a weighting coefficient, a log compression curve, a diffraction curve, a ringdown-gain control (RGC) curve, a time-gain compensation (TGC) factor, and a time-of-flight adjustment. A log compression curve is one possible technique for grayscale or pseudo-color conversion that maps a signal attribute to a pixel attribute. Log compression curves are not necessarily logarithmic and may in fact be a function of a natural log, a static value, a linear expression, a polynomial expression, and/or another mathematical relation. A diffraction correction curve is a method of filtering and reducing diffraction effects in a beam-formed sensing device such as a rotational or solid-state IVUS device. Ringdown-gain control is a form of time gain compensation used to remove image artifacts caused by catheter ringdown. Time-gain compensation is a type of distance-sensitive amplification that provides consistent contrast over a given field-of-view despite rapid signal attenuation as the target moves away from the sensor. U.S. Pat. No. 8,187,191, entitled "SYSTEM AND METHOD FOR EQUALIZING RECEIVED INTRAVASCULAR ULTRASOUND ECHO SYSTEMS," U.S. Patent Publication No. 2010/0174190, entitled "SYSTEM AND METHOD FOR EQUALIZING RECEIVED INTRAVASCULAR ULTRASOUND ECHO SYSTEMS," U.S. Patent Publication No. 2012/0220874, entitled "SYSTEM AND METHOD FOR EQUALIZING RECEIVED INTRAVASCULAR ULTRASOUND ECHO SYSTEMS," and U.S. Patent Application Publication No. 2014/0056099, entitled "SYSTEM AND METHOD FOR FOCUSING ULTRASOUND IMAGE DATA," disclose IVUS data collection and focusing in a phased array synthetic aperture IVUS system in more detail and are hereby incorporated by reference in their entirety. It is understood that these operating parameters are merely exemplary and, in other embodiments, the parameter module 306 modifies other suitable operating parameters.

In some embodiments, the parameter module 306 determines which operating parameters to modify and their corresponding values based in part on the user's mode selection and in part on other environmental data such as previous mode selections, user preferences, the operative course of a procedure, patient information, correlated medical data from other modalities, status indicators, sensing device identifiers, and/or other data that describes the operating environment. By fine-tuning operating parameters based on other available environmental data, the parameter module 306 can further optimize and enhance a structure of interest without requiring any further user input. In some embodiments, the module 306 responds to changes in the environment in real time without prompting. Thus, the parameter module 306 may perform dynamic adaptive enhancement of operating parameters in response to changing conditions.

Various embodiments will now be described. It is understood that the described embodiments are merely exemplary and are non-limiting. In some embodiments, the parameter module 306 determines a set of operating parameters based on received medical sensing data. The medical data may be the current data being processed or any other suitable medical data, may correspond to the current modality or any other suitable modality, and may be unprocessed or processed medical data. In that regard, in one such embodiment, the parameter module 306 receives unprocessed medical imaging data, such as raw IVUS, pressure, or flow data, from a modality acquisition component 308 (e.g., an IVUS acquisition component, an FL-IVUS acquisition component, another modality acquisition component, etc.). In another such embodiment, the parameter module 306 receives processed medical imaging data, such as focused IVUS data or processed pressure or flow data, from a modality workflow component 310 (e.g., an IVUS workflow component, an FL-IVUS workflow component, a pressure workflow component, a flow workflow component, another modality workflow component, etc.).

For example, in one embodiment, the parameter module 306 receives IVUS sensing data indicating an area of suspected calcification. Based in part on the IVUS data, the parameter module 306 determines an operating parameter that improves the grayscale contrast the corresponding area to improve characterization of the arterial tissue. In another exemplary embodiment, the parameter module 306 receives IVUS sensing data containing a hot spot caused by a strong ultrasonic reflector such as a coronary stent. In response to a user selection, the parameter module 306 determines an operating parameter that enables a fluid flow analysis to detect stent malapposition. In another exemplary embodiment, the parameter module 306 receives IVUS sensing data, determines the size of the surrounding vasculature from the imaging data, and sets an operating parameter corresponding to focal distance accordingly. In a further example, the list builder module uses the border-detection process to identify a segment of vasculature corresponding to the IVUS data and configures an operating parameter according to the particular vasculature segment. In a further example, the list builder module 304 identifies a plaque structure from IVUS imaging data, and applies an algorithm to the imaging data to estimate a degree of calcification. The list builder module then sets an operating parameter to enhance identification and analysis of the type of plaque. In another exemplary embodiment, the parameter module 306 receives radiographic data indicating an anatomical location of an IVUS catheter. From the radiographic data, the parameter module 306 determines an operating parameter based on anatomical structures located near the catheter tip.

In some embodiments, the parameter module 306 receives a status indicator from a component of the system 100. Exemplary status indicators correspond to system states, system readiness, readiness of an attached device, device identifiers and/or other suitable indicators. For example, the status indicator may include a sensing device identifier that contains the make and model of a sensing device coupled to the system 100. A family of sensing devices may have a particular interface specification that defines device characteristics such as a communications protocol, data signaling parameters, operating voltages, and processing coefficients. Particular devices within a device family may also have further device characteristics such as sensitivity adjustments unique to that particular device. To determine the family and/or device-specific characteristics, the parameter module 306 may use the sensing device identifier to query a sensing device database 318. In an exemplary embodiment, the parameter module 306 receives a sensing device identifier that identifies the attached device as an Eagle Eye® (registered trademark of Volcano Corporation) IVUS imaging catheter. Using the device identifier, the parameter module 306 retrieves an interface specification for the Eagle Eye® family of devices from the device database 318. In the example, the attached imaging catheter has been tested during manufacturing and the sensitivities of the catheter transceivers have been recorded. Using the device identifier, the parameter module 306 retrieves a set of sensitivity adjustments particular to the attached catheter. The parameter module 306 determines operating parameters for the focusing of the echo data based on the interface specification and the sensitivity adjustments. In a further exemplary embodiment, the parameter module 306 receives a sensing device identifier and from the identifier determines that the associated catheter has a 64-element IVUS array and supports apertures of 8 to 16 elements. The parameter module 306 may determine operating parameters such as apodization coefficients and/or time of flight adjustments for one, some, or all of the supporter aperture sizes.

The above operating parameters are merely non-limiting examples of the optimization the parameter module 306 can perform in response to the user-selected mode and other pertinent data. In further embodiments, the parameter module 306 determines values for other operating parameters in order to enhance the operation of the system 100. Once determined, the adaptive interface module 302 provides the set of operating parameters for use by the system 100 in processing the medical sensing data.

Figure 4:
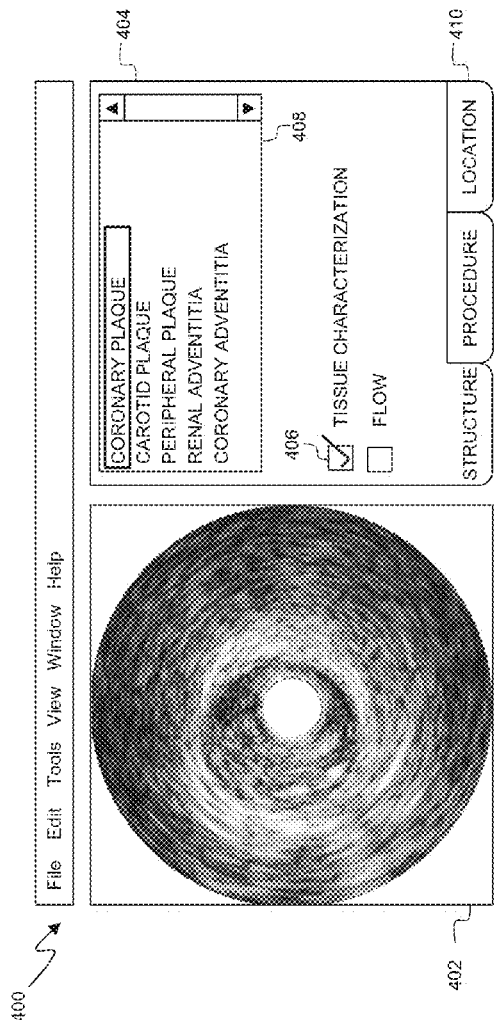
FIG. 4 is a diagram of an exemplary adaptive user interface for control of the medical system of FIGS. 1A, 1B, and 1C according to some embodiments of the present disclosure.

FIG. 4 is a diagram of an exemplary adaptive user interface for control of the medical system of FIGS. 1A, 1B, and 1C according to some embodiments of the system. The user interface 400 may be displayed on a user display such as the user display 324 described with reference to FIG. 3. The user interface 400 represents one possible arrangement for displaying the information presented by the multi-modality processing system 100 and more specifically presented by the adaptive interface module 302 of the system. One skilled in the art will recognize that alternate arrangements are both contemplated and provided for.

In the illustrated embodiment, the user interface 400 includes one or more display panes 402 for displaying current medical sensing data. Examples of medical sensing data include IVUS data, forward-looking IVUS (FL-IVUS), fractional flow reserve (FFR) determination, a coronary flow reserve (CFR) determination, optical coherence tomography (OCT) data, and trans-esophageal echocardiography data. The user interface 400 also includes one or more mode selection panes 404. The mode selection pane 404 may offer one or more user-selectable mode options. Mode options may be presented via checkboxes 406, exclusive and non-exclusive lists 408, radio buttons, and other suitable interface schemes. The mode options are selectable by a user, and doing so creates a mode selection that is provided by the user interface 400 to a corresponding component of the medical system. In the illustrated embodiment, the mode selection pane 404 presents the mode options in categories presented as tabs 410, although this is merely exemplary and other arrangements including dropdown menus, toolbars, trees, and other suitable arrangements are provided for. Upon user selection of a category, a list of corresponding mode options may be presented.

Figure 5:
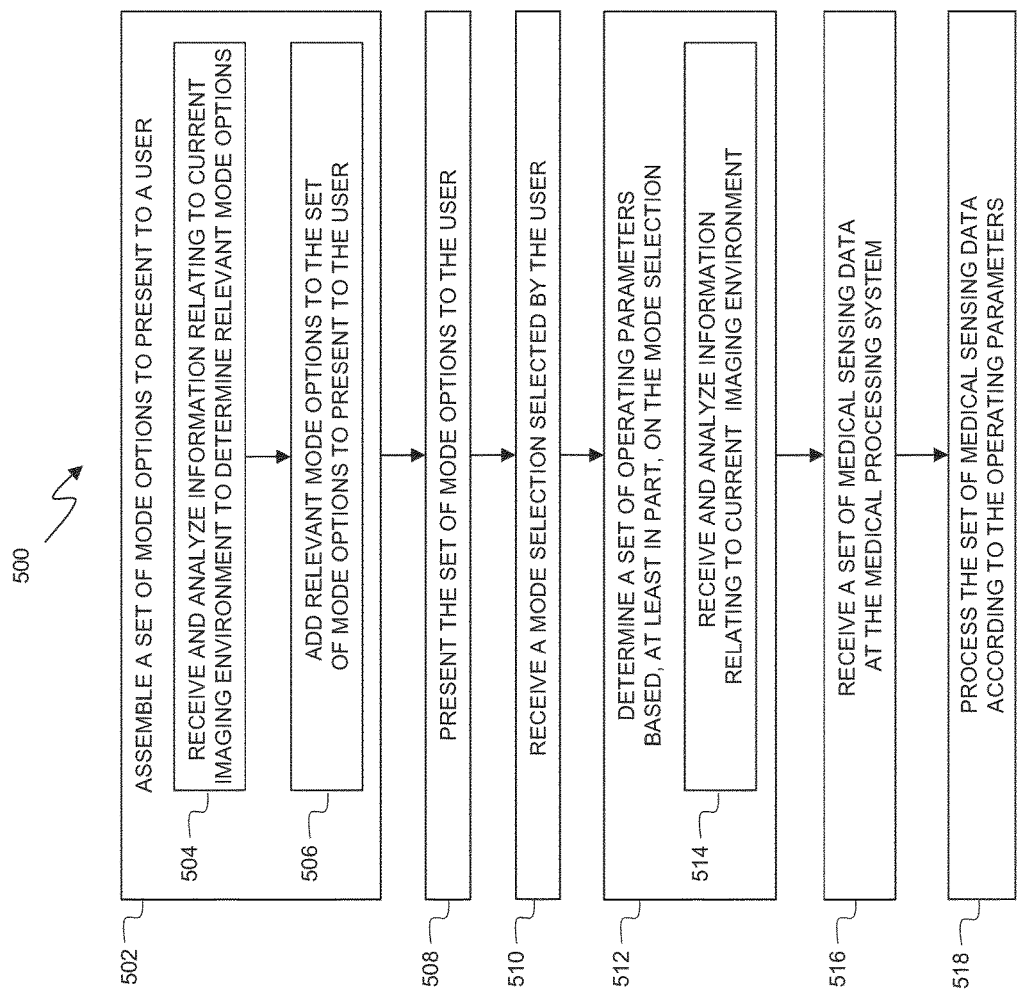
FIG. 5 is a flow diagram of a method of presenting an adaptive user interface and responding to a user selection within a medical system according to some embodiments of the present disclosure.

FIG. 5 is a flow diagram of a method 500 of presenting an adaptive user interface and responding to a user selection within a medical system according to some embodiments of the present disclosure. It is understood that additional steps can be provided before, during, and after the steps of method 500, and some of the steps described can be replaced or eliminated for other embodiments of the method.

In block 502, a set of imaging mode options is assembled for presenting to a user. Exemplary imaging modes may by characterized by one or more of a target structure, a vasculature segment, a vasculature type, a tissue type, a gross anatomical location, a procedure, a focal distance, and/or other suitable criteria. For example, in an embodiment, imaging mode options correspond to target structures of interest (e.g., coronary plaque, carotid plaque, peripheral plaque, coronary adventitia, renal adventitia, stent, etc.). In a further example, the set contains mode options corresponding to segments of the vasculature (e.g., left anterior descending artery, left circumflex artery, left main coronary artery, right coronary artery, etc.). In another example, the set including imaging mode options corresponding to vasculature type (e.g., coronary vasculature, renal vasculature, peripheral vasculature, bifurcation, etc.). In another example, the set contains mode options corresponding to surgical procedures (e.g., coronary imaging, balloon angioplasty, stent placement, plaque ablation, renal tissue ablation, etc.).

Referring to block 504, in some embodiments, assembling a set of imaging mode options to present includes receiving and analyzing information pertaining to the current imaging environment to determining relevant imaging modes. This may include the analysis disclosed with reference to FIG. 3. In various embodiments, this environmental information includes previous user mode selections, user preferences, the operative course of a procedure, patient information, correlated medical data from other modalities, status indicators, sensing device identifiers, and/or other data that describes the imaging environment. In block 506, the relevant imaging mode options are added to the set of mode options to present to the user.

In block 508, the set of imaging mode options is presented to the user. In block 510, a mode selection made by the user is received. In block 512, a set of operating parameters is determined based, at least in part, on the mode selection. Operating parameters for IVUS imaging modes may include catheter parameters such as ultrasonic waveform parameters, emitter power, amplification, and emitter/receiver patterns, and/or may include processing parameters such as gain, sensitivity, sampling rates, grayscale or pseudo-color conversion factors, apodization coefficients, weighting coefficients, log compression curves, time-gain compensation (TGC) factors, time-of-flight adjustments, signal filtering parameters, signal filter types. In some embodiments, operating parameters may enable one of a fluid flow analysis and a tissue characterization process.

In some embodiments, the determining of the set of operating parameters includes receiving and analyzing other information pertaining to the current imaging environment, as illustrated by block 514. This information may include information such as previous mode selections, user preferences, the operative course of a procedure, patient information, correlated medical data from other modalities, status indicators, sensing device identifiers, and/or other information that describes the operating environment. The analysis may include one or more of the processes disclosed with reference to FIG. 3.

In block 516, a set of medical sensing data such as IVUS ultrasound echo data is received. The set of medical sensing data is processed according to the operating parameters in block 518.

Although illustrative embodiments have been shown and described, a wide range of modification, change, and substitution is contemplated in the foregoing disclosure and in some instances, some features of the present disclosure may be employed without a corresponding use of the other features. Further, as described above, the components and extensions described above in association with the multi-modality processing system may be implemented in hardware, software, or a combination of both. The processing systems may be designed to work on any specific architecture. For example, the systems may be executed on a single computer, local area networks, client-server networks, wide area networks, internets, hand-held and other portable and wireless devices and networks. It is understood that such variations may be made in the foregoing without departing from the scope of the present disclosure. Accordingly, it is appropriate that the appended claims be construed broadly and in a manner consistent with the scope of the present disclosure.

What is claimed is:

1. An intravascular system, comprising:
an intravascular device operable to obtain intravascular data while positioned within a vessel of a patient, the intravascular device including a flexible elongate member and an imaging element coupled to a distal portion of the flexible elongate member; and
a computing device in communication with the intravascular device, the computing device operable to:
receive a selection of a mode associated with the intravascular data from among a plurality of mode options, wherein the selected mode is representative of at least one of a target structure, a vasculature segment, a vasculature type, a tissue type, a gross anatomical location, a surgical procedure, or a focal distance associated with the intravascular data;
determine an intravascular device parameter based on the selected mode, wherein the intravascular device parameter is associated with operation of the imaging element to obtain the intravascular data;
receive the intravascular data obtained by the imaging element while the intravascular device is positioned within the vessel of the patient;
process the intravascular data; and
output, to a display device in communication with the computing device, a graphical representation of the processed intravascular data.

2. The system of claim 1, wherein the intravascular device parameter includes at least one of an ultrasonic waveform parameter, an emitter power, an amplification parameter, or an emitter/receiver pattern.

3. The system of claim 1, wherein the computing device is operable to process the intravascular data by:
   determining a processing parameter based on the selected mode; and
   processing the intravascular data based on the processing parameter.

4. The system of claim 3, wherein the processing parameter includes at least one of a gain parameter, a sensitivity parameter, a sampling rate, a grayscale conversion parameter, a pseudo-color conversion factor, a diffraction correction curve, a ringdown-gain control value, an apodization coefficient, a weighting coefficient, a log compression curve, a time-gain compensation factor, a time-of-flight adjustment, a signal filtering parameter, or a signal filter type.

5. The system of claim 1, wherein the computing device is operable to:
   determine the plurality of mode options; and
   output, to the display device, the plurality of mode options.

6. The system of claim 5, wherein computing device is operable to determine the plurality of mode options by:
   identifying relevant mode options based on at least one of a previous mode selection, a user preference, an operative course of a medical procedure, patient information, the intravascular data, medical sensing data, a status indicator, or an intravascular device identifier.

7. An intravascular system, comprising:
   an intravascular device operable to obtain intravascular data while positioned within a vessel of a patient, the intravascular device including a flexible elongate member and an imaging element coupled to a distal portion of the flexible elongate member; and
   a computing device in communication with the intravascular device, the computing device operable to:
      receive the intravascular data obtained by the intravascular device while the intravascular device is positioned within the vessel of the patient;
      receive a selection of mode associated with the imaging element from among a plurality of mode options, wherein the selected mode is representative of at least one of a target structure, a vasculature segment, a vasculature type, a tissue type, a gross anatomical location, a surgical procedure, or a focal distance associated with the intravascular data;
      determine a processing parameter based on the selected mode;
      process the intravascular data based on the processing parameter; and
      output, to a display device in communication with the computing device, a graphical representation of the processed intravascular data.

8. The system of claim 7, wherein the processing parameter includes at least one of a gain parameter, a sensitivity parameter, a sampling rate, a grayscale conversion parameter, a pseudo-color conversion factor, a diffraction correction curve, a ringdown-gain control value, an apodization coefficient, a weighting coefficient, a log compression curve, a time-gain compensation factor, a time-of-flight adjustment, a signal filtering parameter, or a signal filter type.

9. The system of claim 7, wherein the computing device is operable to determine an intravascular device parameter based on the selected mode, wherein the intravascular device parameter is associated with operation of the imaging element to obtain the intravascular data.

10. The system of claim 9, wherein the intravascular device parameter includes at least one of an ultrasonic waveform parameter, an emitter power, an amplification parameter, or an emitter/receiver pattern.

11. The system of claim 7, wherein the computing device is operable to:
    determine the plurality of mode options; and
    output, to the display device, the plurality of mode options.

12. The system of claim 11, wherein the computing device is operable to determine the plurality of mode options by:
    identifying relevant mode options based on at least one of a previous mode selection, a user preference, an operative course of a medical procedure, patient information, the intravascular data, medical sensing data, a status indicator, or an intravascular device identifier.

* * * * *